United States Patent
Schwarz et al.

(10) Patent No.: US 7,256,356 B2
(45) Date of Patent: Aug. 14, 2007

(54) APPARATUS AND METHOD FOR COUPLING A MODULE ASSEMBLY IN A HOUSING

(75) Inventors: Reinhard Schwarz, Eggelsberg (AT); Helmut Pall, Hochberg (AT)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 165 days.

(21) Appl. No.: 10/677,142

(22) Filed: Sep. 30, 2003

(65) Prior Publication Data

US 2005/0068769 A1 Mar. 31, 2005

(51) Int. Cl.
*H05K 7/02* (2006.01)
*H05K 7/14* (2006.01)

(52) U.S. Cl. .............. 174/541; 174/542; 361/219

(58) Field of Classification Search ........... 362/219; 174/520, 541, 542
See application file for complete search history.

(56) References Cited

U.S. PATENT DOCUMENTS

| | | | |
|---|---|---|---|
| 3,774,039 A | 11/1973 | Price | 350/552 |
| 3,996,476 A | 12/1976 | Lazzara | 250/563 |
| 5,949,020 A * | 9/1999 | Mitchell et al. | 174/40 CC |
| 5,998,785 A | 12/1999 | Beck et al. | 250/239 |
| 6,025,963 A | 2/2000 | Hippenmeyer et al. | 359/819 |
| 6,035,491 A * | 3/2000 | Hartigan et al. | 16/342 |
| 6,175,106 B1 | 1/2001 | Buitkamp et al. | 250/221 |
| 6,538,891 B1 * | 3/2003 | He et al. | 361/704 |

OTHER PUBLICATIONS

"MiniSafe MS4600 Series Safety Light Curtain", *MiniSafe MS4600 Installation and Operating Manual*, (Jul. 8, 1999), 1-39.

\* cited by examiner

*Primary Examiner*—Hung V. Ngo
(74) *Attorney, Agent, or Firm*—Catherine Klima-Silberg; William R. Walbrun

(57) ABSTRACT

An assembly, such as a sensor assembly, includes an optional housing having an inner surface and an outer surface where the housing includes housing connecting features. The assembly further includes a module assembly with at least one resilient member, and an elongate member coupled with the at least one resilient member. The module assembly and the elongate member are disposed within the housing where the elongate member is coupled with the housing with the housing connecting features.

18 Claims, 3 Drawing Sheets

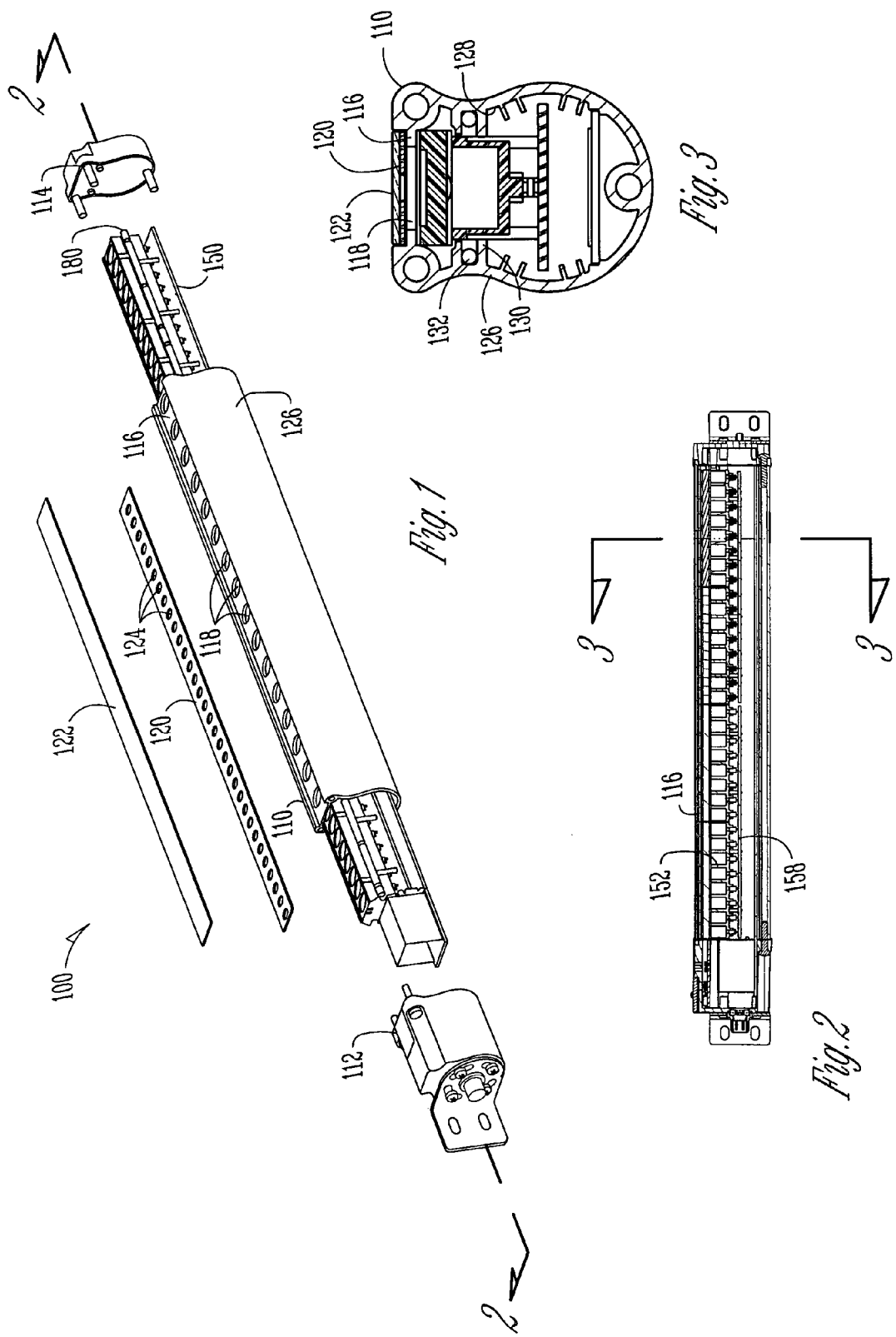

APPARATUS AND METHOD FOR COUPLING A MODULE ASSEMBLY IN A HOUSING

TECHNICAL FIELD

The present invention relates generally to coupling features for a module assembly.

BACKGROUND

Light curtains have a number of applications, such as to perform a variety of measurement and inspection functions. Light curtains are used to size parts, verify part features such as edges, holes and other distinguishing characteristics, and for verification of part ejection. Light curtains may also be used on many types of industrial machinery, such as punches, presses, drills, saws, etc., in order to sense the presence of foreign objects or as part of security or safety systems.

Light curtain devices typically employ a number of light beams that are disposed to fan out across a designated location in a production line. Typically, such devices employ a plurality of active elements on both sides of the area to be monitored. For example, a plurality of light generators, each of which generates a light beam or column, may be disposed on one side of the monitored area, and a corresponding plurality of light detectors may be disposed on the other side of the monitored area. The interruption of one or more of the light columns thus indicates, for example, the presence of a part at the monitored area, and tracking of which light columns are interrupted can be used, for example, to determine the type or orientation of the part at the monitored location.

Therefore, the alignment of the light curtain is important. However, use of the light curtain over an extended period of time or in a warm factory setting can place thermal stress on one or more of the components of the light curtain potentially affecting the disposition of the components of or within the light curtain relative to one another. This may further affect the alignment of the light curtains resulting in additional alignment procedures, or a decrease in range of the light curtain.

Accordingly, what is needed is a light curtain with improved alignment that is consistent over time and throughout changes in the environment in which it operates.

SUMMARY

An assembly, such as a sensor assembly, includes a housing having an inner surface and an outer surface where the housing includes housing connecting features. The assembly further includes a module assembly with at least one resilient member, and an elongate member coupled with the at least one resilient member. The module assembly and the elongate member are disposed within the housing where the elongate member is coupled with the housing with the housing connecting features.

Several options exist for the sensor assembly. For example, in one option, the elongate member and the housing are each formed of material having substantially similar thermal properties. In another option, the elongate member is slidable disposable within the housing. Still further, in another option, the resilient member includes a resilient spring arm that extends outwardly from the module assembly.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1 is an exploded perspective view illustrating a sensor assembly constructed in accordance with one embodiment.

FIG. 2 is a cross-sectional view illustrating a sensor assembly constructed in accordance with one embodiment.

FIG. 3 is a cross-sectional view illustrating a sensor assembly constructed in accordance with one embodiment.

DESCRIPTION OF THE EMBODIMENTS

Figure 4A:
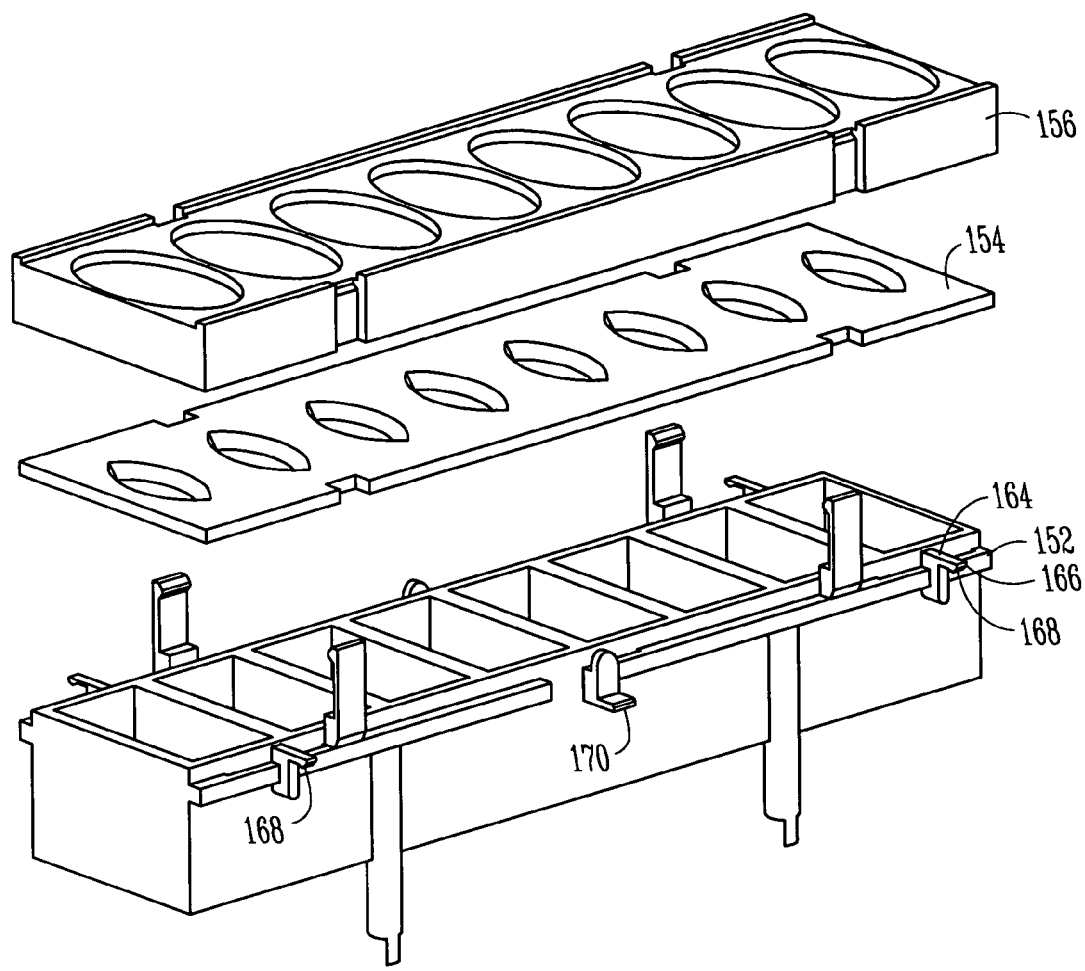
FIG. 4A illustrates an exploded perspective view of a portion of the sensor assembly in accordance with one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIGS. 1–3 illustrate a sensor assembly 100. The sensor assembly 100 includes a sensor housing 110, a module assembly 150, and a support member 180. The housing 110, in one option, is an elongate structure that is formed, in one example, by extrusion. The housing 110 is formed of a metal, such as aluminum, and the material of the housing 110 has a first rate of thermal expansion.

The housing 110 includes two end portions 112, 114, respectively which close off the ends of the housing 110. The housing includes a front portion 116 which includes a plurality of openings 118 therein. The term "front" is used only for the terms of the description of this drawing. It should be noted that the housing can be disposed in other manners where the surface may not form the "front." Coupled with the surface 116 is an adhesive member 120. The adhesive member 120 includes a plurality of openings 124 therein which are aligned with the openings 118. In one embodiment, the adhesive member 120 is a piece of double-sided tape. However, it should be noted that the adhesive member 120 can take on other forms such as a fastener. The adhesive member 120 is used to secure member 122 to surface 116 of the housing 110. Other forms of fastening the member 122 to the surface 116 can also be implemented.

The housing 110 includes an outer surface 126 and an inner surface 128, as illustrated in FIG. 3. In one option, the inner surface 128 of the housing 110 includes housing coupling features 130 therein. In one option, the housing coupling features 130 include one or more slots 132 formed within the housing 110 on the inner surface 128. Alternatively, the housing coupling features 130 form one or more arms extending from the inner surface 128 of the housing 110. The coupling features 130, in one option, are recessed or elongate and are longitudinally aligned with a longitudinal axis of the housing. The coupling features allow for the module assembly 150 to be coupled therein.

Figure 4B:
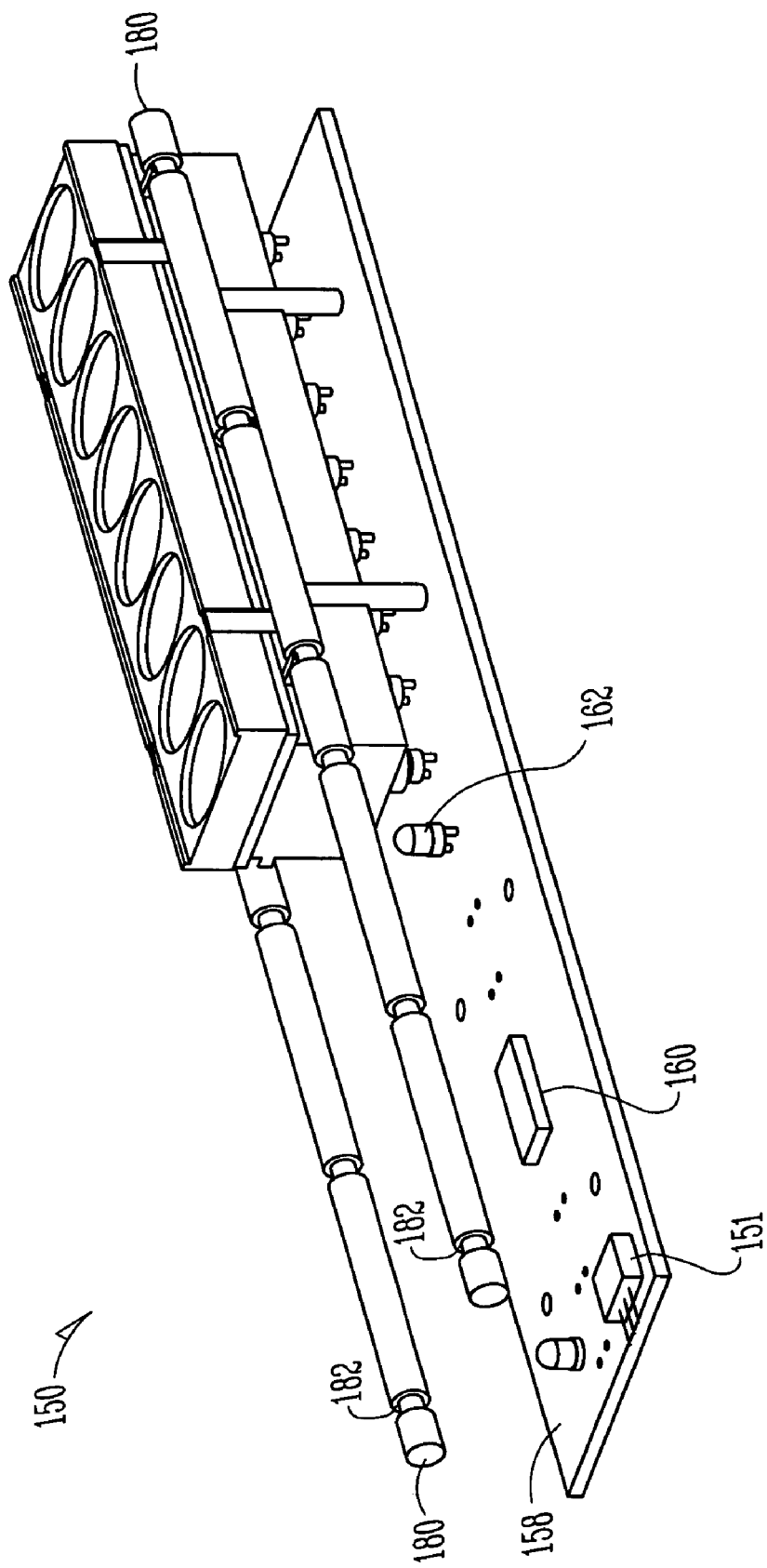
FIG. 4B illustrates an exploded perspective view of a portion of the sensor assembly in accordance with one embodiment.

Referring to FIGS. 4A and 4B, the module assembly 150 includes a lens carrier 152, a cover 154, and a lens module 156. The lens carrier 152 includes features coupled therewith to attach the cover 154 and a lens module 156 thereto. The cover 154 includes a plurality of openings therein to allow light to access the lenses of the lens module 156. The lens carrier 152 further includes features allowing the module assembly 150 to be coupled with a printed circuit board 158 which forms part of the module assembly 150. The printed circuit board 158 includes one or more electronic components 160 coupled thereto. The module assembly 150 further includes at least one light source 162. In another option, the module assembly 150 includes, in addition to or in alternative to the light source 162, a receiving component for sensing the presence of light. In one option, multiple module assemblies are provided and include connectors disposed between the module assemblies. In one option, the connector 151 includes connecting features that are substantially parallel with a longitudinal axis of the module assembly.

The module assembly 150 further includes features that allow it to be coupled within the housing 110 (FIG. 1), in conjunction with other components. In one option, the module assembly 150 includes at least one resilient member 164. The resilient member 164 is in one option formed adjacent to outer portions of the module assembly 150. In one embodiment, the resilient member 164 includes one or more resilient arms 166, for example, a resilient spring arm. In one option, the resilient arms 166 include at least one upper arm 168, and at least one lower arm 170, as illustrated in FIG. 4A. The terms "upper" and "lower" are not intended to limit the placement of the arms, but merely describe the relative relationship of the arms, as illustrated in FIG. 4A. Other dispositions for the resilient members and/or resilient arms are also considered within the scope of this application. It should be noted that the resilient member 164 can take on a number of formats. For example, the at least one resilient member 164 can also form a pocket, or a recess, a hook, a catch, a clasp, a groove, a projection having a variety of cross-sections, or the like.

In another option, the at least one resilient member 164 allows for it to be snap-fittedly coupled with another member, such as an elongate isolation member, as discussed further below. In one option, the resilient member 164 extends outwardly from a portion of the module assembly 150 and has a similar material as the module assembly 150. In yet another option, the at least one resilient member 164 forms a finger-like projection having a small hook on the end. In another option, the resilient member 164 is not entirely rigid, in that it has some give to it. The resilient arms 166, in one option, are offset from one another. For example, in one option, an upper arm 168 is offset from the lower arm 170, as illustrated in FIG. 4A.

Referring to FIG. 4B, at least one member 180 is coupled with the module assembly 150. In one option, the member 180 is elongate and is an isolation member, and it is disposed between a portion of the module assembly 150 and the housing 110 (FIG. 1). Optionally, the member 180 extends along an outer side portion of the module assembly 150 and/or has a substantially similar length as the module assembly 150. In one option, the member 180 is formed of a material having a rate of thermal expansion that is substantially similar to that of the material used for the housing 110 (FIG. 1). In another option, the member 180 is an elongate substantially tubular structure. In still yet another option, the member 180 includes one or more portions that engage the at least one resilient member 164. In one option, the one or more portions include a recess 182 that couples with, for example, the resilient arms 166, where a resilient arm is disposed within the recess 182. In yet another option, the portions allow for rotatable movement of the member 180 relative to the module assembly 150, without longitudinal movement of the member 180 relative to the module assembly 150. The member 180, in one option, is thermally expandable independent of the module assembly 150.

The member 180 allows for the module assembly 150 to be coupled within the housing 110 in such a manner to allow for thermal expansion of the coupling feature, for example, the member 180, without interference with the module assembly 150 from thermal expansion of the housing 110. In one option, the member 180 is disposed within coupling features of the housing 110, as illustrated in FIG. 2. The member 180, during assembly of the module assembly within the housing 110, is disposed within, for example, the elongate slot of the housing 110, for example, by sliding the module assembly 150 within the housing 110. The member 180 is disposed between a portion of the module assembly 150 and the housing 110.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein, is intended merely to better illuminate the invention and does not pose a limitation on the scope of the invention unless otherwise claimed. No language in the specification should be construed as indicating any non-claimed element as essential to the practice of the invention.

It is to be understood that the above description is intended to be illustrative and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims along with the full scope of equivalents to which such claims are entitled.

What is claimed is:

1. An assembly comprising:
   a module assembly including one or more electronic components;
   at least one resilient member coupled with the module assembly, the at least one resilient member is at an outer portion of the module assembly;

at least one elongate isolation member coupled with the at least one resilient member; and a housing, the module assembly disposed within and coupled with the housing and the at least one elongate isolation member coupling the module assembly with the housing.

2. The assembly as recited in claim 1, wherein the at least one elongate isolation member includes one or more recesses therein, and the at least one resilient member is a spring arm disposed within the at least one recess.

3. The assembly as recited in claim 1, wherein the at least one elongate isolation member has substantially similar thermal expansion properties as the housing.

4. The assembly as recited in claim 1, wherein the at least one elongate isolation member is rotatable relative to the module assembly.

5. An assembly comprising:
a housing having an inner surface and an outer surface, the housing having housing connecting features therein;
a module assembly including at least one resilient member;
an elongate member coupled with the at least one resilient member, the elongate member coupled with the housing with the housing connecting features; and
the module assembly and the elongate member disposed within the housing.

6. The assembly as recited in claim 5, wherein the housing is formed of a first material and the elongate member is formed of a second material, and the first material and the second material have substantially similar rates of thermal expansion.

7. The assembly as recited in claim 5, wherein the housing connecting features include an elongate slot on the inner surface of the housing.

8. The assembly as recited in claim 5, wherein at least one resilient member comprises at least one resilient spring arm extending outwardly from the module assembly.

9. The assembly as recited in claim 5, wherein the elongate member has a member length, the module assembly has an assembly length, and the member length is substantially similar to the assembly length.

10. An assembly comprising:
an elongate housing;
a module assembly including electrical components and circuitry, the module assembly disposed within the housing;
an elongate member disposed between the module assembly and the housing, the elongate member coupled with a portion of the housing; and
means for coupling the elongate member with the module assembly.

11. The assembly as recited in claim 10, wherein the housing is formed of a first material and the elongate member is formed of a second material, and the first material and the second material have substantially similar rates of thermal expansion.

12. The assembly as recited in claim 10, further comprising means for coupling the elongate member with the housing.

13. The assembly as recited in claim 10, further comprising a plurality of module assemblies, each module assembly having a longitudinal axis, a connector having connecting features substantially parallel with the module assembly longitudinal axis.

14. A method comprising:
forming one or more resilient members adjacent to outer portions of a module assembly, the module assembly including electronic circuitry and electronic components;
coupling an elongate member with one or more resilient members of the module assembly;
disposing the elongate member and the module assembly within a housing; and
coupling the elongate member with a portion of the housing.

15. The method as recited in claim 14, wherein coupling the elongate member with the portion of the housing includes coupling the elongate member directly with the portion of the housing and sliding the elongate member within a slot formed within the housing.

16. The method as recited in claim 14, wherein coupling an elongate member with the one or more resilient members includes disposing a resilient arm of the module assembly within a recess of the elongate member.

17. The method as recited in claim 14, wherein coupling an elongate member with one or more resilient members includes snap-fittedly coupling the elongate member with one or more resilient members.

18. The method as recited in claim 14, wherein coupling the elongate member with the portion of the housing includes coupling the elongate member having substantially similar thermal properties as the housing.

* * * * *